United States Patent [19]
Bonitz

[11] Patent Number: 5,974,888
[45] Date of Patent: Nov. 2, 1999

[54] ULTRASONIC ANGLE-BEAM PROBE AND METHOD FOR OPERATING THE ANGLE-BEAM PROBE

[75] Inventor: Frank Bonitz, Neunkirchen, Germany

[73] Assignee: ABB Reaktor GmbH, Mannheim, Germany

[21] Appl. No.: 08/891,515

[22] Filed: Jul. 11, 1997

[30] Foreign Application Priority Data

Jul. 11, 1996 [DE] Germany ............. 196 27 957

[51] Int. Cl.⁶ .............. G01N 29/06; G01N 29/10
[52] U.S. Cl. ................. 73/624; 73/625; 73/628
[58] Field of Search .............. 73/597, 598, 599, 73/600, 620, 622, 624, 625, 626, 627, 628, 632, 641, 642, 644

[56] References Cited

U.S. PATENT DOCUMENTS

| | | | |
|---|---|---|---|
| 3,962,908 | 6/1976 | Joy | 73/636 |
| 4,275,598 | 6/1981 | Engl | 73/622 |
| 4,435,984 | 3/1984 | Gruber | 73/628 |
| 4,680,967 | 7/1987 | Rost | 73/628 |
| 5,094,108 | 3/1992 | Kim et al. | 73/627 |
| 5,549,001 | 8/1996 | Brokowski et al. | 73/597 |
| 5,814,731 | 9/1998 | Alexander et al. | 73/644 |

*Primary Examiner*—Hezron Williams
*Assistant Examiner*—Rose M. Miller
*Attorney, Agent, or Firm*—Herbert L. Lerner; Laurence A. Greenberg

[57] ABSTRACT

An ultrasonic angle-beam probe and a method for operating the angle-beam probe include an approach wedge to be driven into a gap. The overall height of the probe sets limits which preclude testing starting from a specific gap width. At least two approach wedges are provided in order to give the angle-beam probe a testing sensitivity that is maintained even in the case of a reduced overall height. A device is provided which can be assigned to a pulse generator, a sound evaluator or a connecting element to a sound transducer, in order to influence a sound echo time.

2 Claims, 2 Drawing Sheets

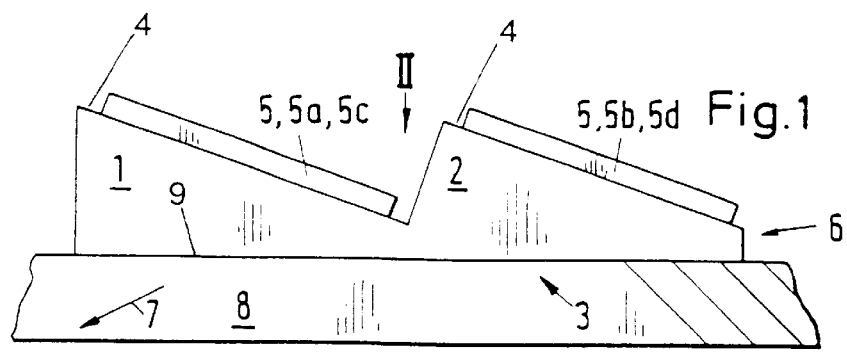
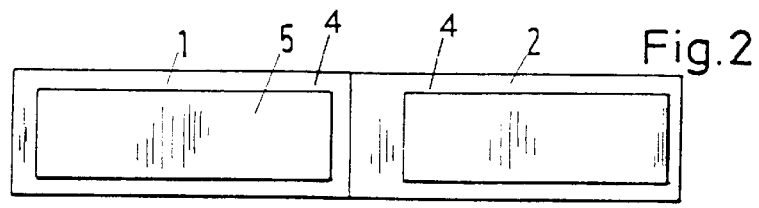
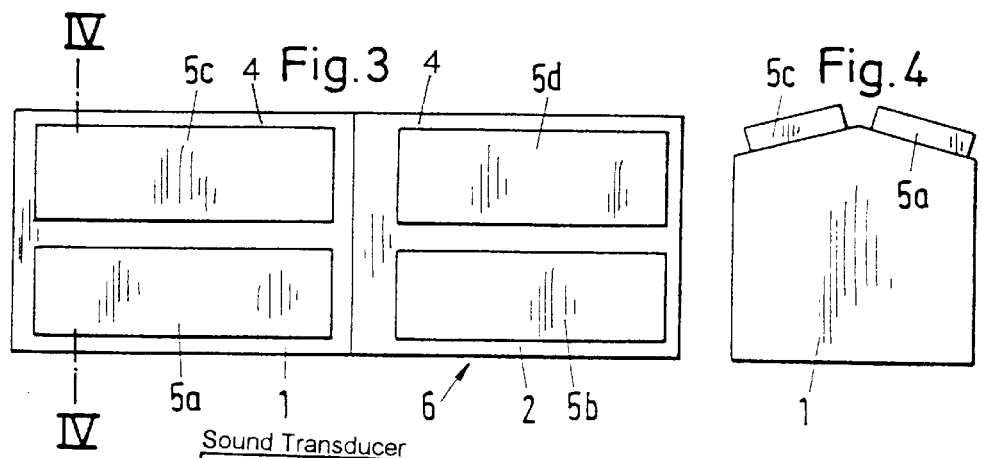
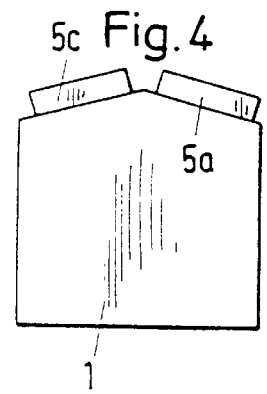
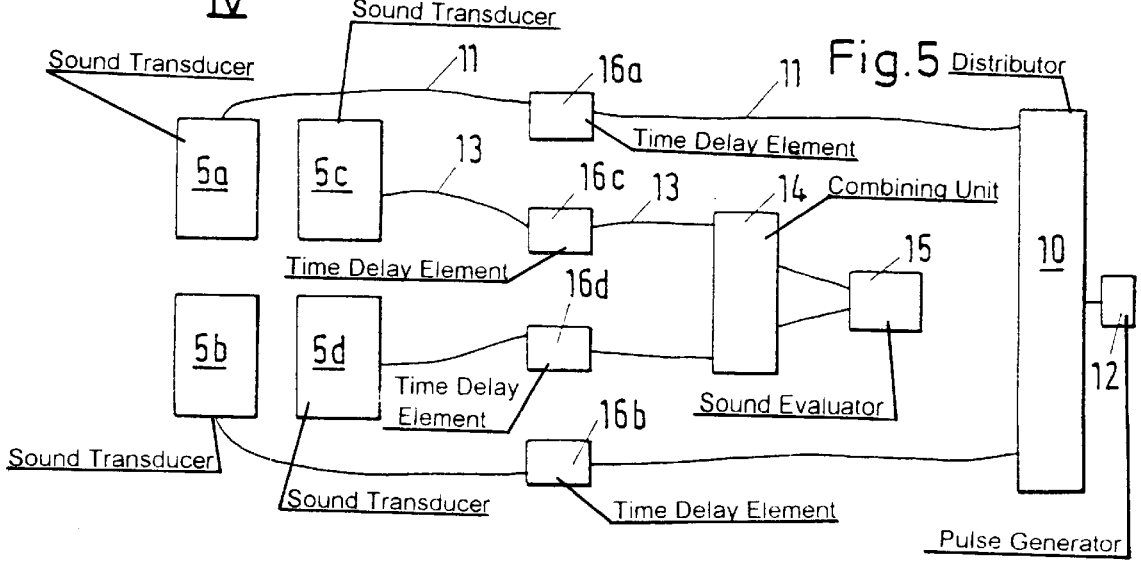

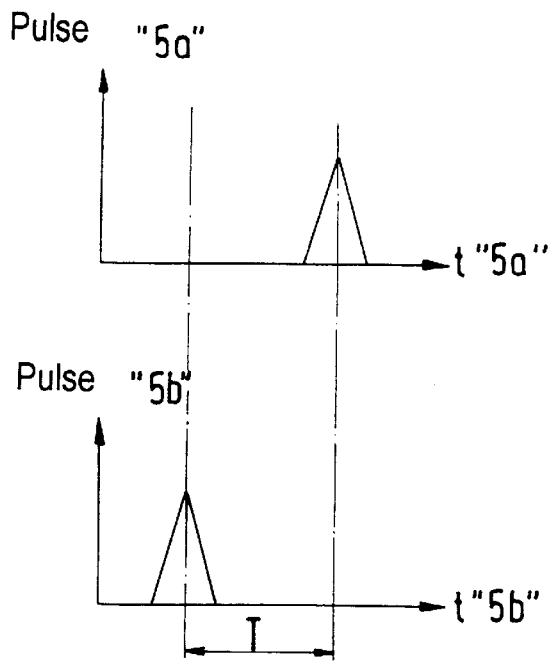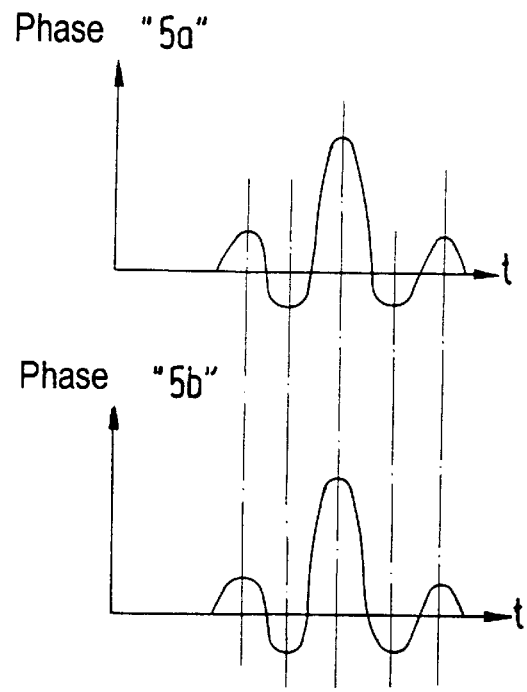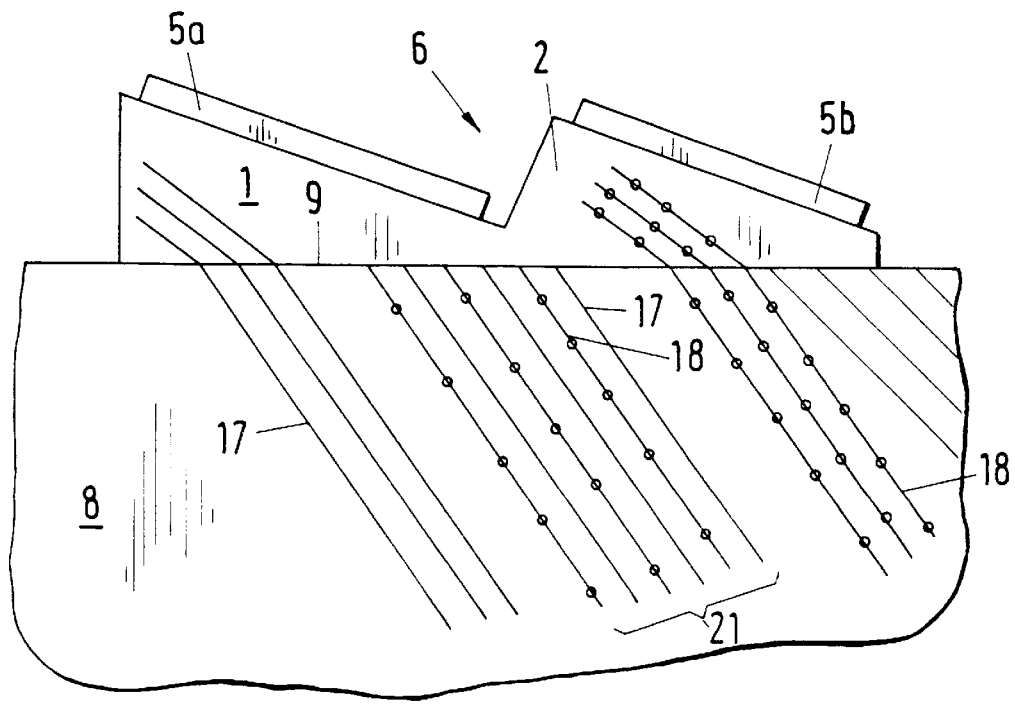

ULTRASONIC ANGLE-BEAM PROBE AND METHOD FOR OPERATING THE ANGLE-BEAM PROBE

BACKGROUND OF THE INVENTION

Field of the Invention

The invention relates to an ultrasonic angle-beam probe having an approach wedge with a wedge surface that carries at least one sound transducer that is connected to a pulse generator and/or a sound evaluator. The invention also relates to a method for operating an ultrasonic angle-beam probe.

Such an angle-beam probe is known from page 238 of the book entitled "Werkstoffprufung mit Ultraschall" [Materials Testing by Ultrasound] by J. and H. Krautkramer, 3rd Edition 1975. In addition to a pulse/echo method described therein, such an angle-beam probe can also operate in a transmit/receive mode, wherein the wedge surface is assigned one separate sound transducer each, for transmitting and receiving soundwaves.

In the case of sound transducers of such angle-beam probes, a specific size is necessary to achieve a specific sound field structure, and is expressed in the overall height of the angle-beam probe. If the angle-beam probe is to be inserted in a gap, the overall height sets limits which preclude testing starting from a specific gap width. A reduction in the overall height would entail reducing the size of the sound transducer and thus a reduced testing sensitivity.

SUMMARY OF THE INVENTION

It is accordingly an object of the invention to provide an ultrasonic angle-beam probe and a method for operating the angle-beam probe, which overcome the hereinafore-mentioned disadvantages of the heretofore-known devices and methods of this general type and which provide a probe having a testing sensitivity that is maintained even in the case of a reduced overall height.

With the foregoing and other objects in view there is provided, in accordance with the invention, an ultrasonic angle-beam probe, comprising at least two approach wedges each having a wedge surface; at least one sound transducer disposed on the wedge surface of each of the approach wedges; a pulse generator and/or a sound evaluator connected to at least one sound transducer; and a device connected to at least one sound transducer for influencing an echo time of sound outside a test specimen.

The double-wedge configuration delivers a substantial rise in the testing sensitivity, although the overall height can be kept lower than if the same testing sensitivity is to be delivered with a single approach wedge. A synchronous sound wave is generated in the material of the test specimen from the sound waves of the individual sound transducers by appropriately influencing the echo time of the pulses or sound waves running outside the test specimen. Thus, the sound amplitudes add together to form a larger total amplitude and lead to an increase in the testing sensitivity. The sound waves coming back from the test specimen are also influenced by being delayed before reaching the sound evaluator in such a way that the individual signals can be added.

In accordance with another feature of the invention, the device for influencing the echo time of the sound can be assigned to the sound generator, the sound evaluator or a connecting element to the sound transducer.

In accordance with a further feature of the invention, the approach wedges are disposed as a double wedge one behind another as seen in the direction of sound intromission or acoustic irradiation.

In accordance with an added feature of the invention, the at least one sound transducer includes a sound transducer disposed on each respective approach wedge for operation using a pulse/echo method.

In accordance with an additional feature of the invention, the at least one sound transducer includes two sound transducers disposed on each respective approach wedge for operation using a transmit/receive method.

With the objects of the invention in view, there is also provided a method for operating an ultrasonic angle-beam probe, which comprises irradiating sound by firstly transmitting an initial pulse from the rear sound transducer, transmitting an initial pulse from the front sound transducer after a prescribable time interval, and delaying a received pulse running from the test specimen to the sound evaluator as a function of an angle of the sound intromission or acoustic irradiation.

The delay in the initial pulse takes place with a specific time offset which leads to a synchronous variation in the sound waves with the same phase angle coming from the individual generators.

With the objects of the invention in view, there is additionally provided a method for operating an ultrasonic angle-beam probe, which comprises irradiating the sound by simultaneously transmitting initial pulses of the individual sound transducers, delaying echo times with respect to one another by a prescribable extent, and delaying a received pulse coming from the test specimen to the sound evaluator as a function of an angle of the sound intromission.

The delay in the sound waves emanating from the sound generator takes place in this case on the way from the sound generator to the sound transducer. The degree of delay is a function of the sound intromission angle in both methods.

Other features which are considered as characteristic for the invention are set forth in the appended claims.

Although the invention is illustrated and described herein as embodied in an ultrasonic angle-beam probe and a method for operating the angle-beam probe, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE DRAWINGS

FIG. 1 is a fragmentary, diagrammatic, cross-sectional view of a series-type approach wedge configuration;

FIG. 2 is a plan view as seen in the direction of an arrow II of FIG. 1, with one sound transducer each per approach wedge;

FIG. 3 is a view corresponding to FIG. 2, with two sound transducers each per approach wedge;

FIG. 4 is a sectional view taken along a line IV—IV of FIG. 3;

FIG. 5 is a block diagram of a circuit configuration for controlling an angle-beam probe;

FIGS. 6 and 7 are timing diagrams for influencing a sound echo time; and FIG. 8 is a fragmentary, cross-sectional view of a test specimen with a representation of a course of sound waves therein.

DESCRIPTION OF THE PREFERRED EMBODIMENTS

Referring now to the figures of the drawings in detail and first, particularly, to FIG. 1 thereof, there is seen a cross section through a configuration composed of two approach wedges 1, 2, which are disposed in series and combined to form a double wedge 3. Each approach wedge has a wedge surface 4 that carries a sound transducer 5 for a pulse/echo mode in accordance with FIG. 2, and two sound transducers 5a, 5b, 5c and 5d for a transmit/receive mode in accordance with FIG. 3. The wedge surfaces are inclined in the shape of a roof as is shown in the cross-section according to FIG. 4. A configuration composed of the double wedge and the sound transducers forms an angle-beam probe 6. An arrow 7 indicates the direction of sound intromission or acoustic irradiation into a test specimen 8, with which contact is made by a coupling surface 9 of the angle-beam probe 6.

In the exemplary embodiment according to FIGS. 3, 4 and 5, the sound transducers 5a and 5b, which are constructed as transmitters, are connected over a line 11 with the interposition of a distributor 10, to a pulse generator 12. The sound transducers 5c and 5d, which serve as receivers for signals returning from the test specimen, are each connected over a respective line 13 with the interposition of a combining unit 14, to a sound evaluator 15. Each line 11 leading from the distributor 10 to the sound transducers 5a and 5b is equipped with a respective time-delay element 16a and 16b for influencing the echo time of the initial or transmitted pulses. Furthermore, each line 13 leading from the sound transducers 5c and 5d to the combining unit 14 likewise has a respective time-delay unit 16c and 16d, which serves to influence the echo time of the signals returning from the test specimen 8.

The functioning of the angle-beam probe and the method of operating the probe are described with the aid of FIGS. 6, 7 and 8. In the case of a structure of the angle-beam probe in accordance with FIG. 3, the initial or transmitted pulse emanating simultaneously from the distributor 10 over the lines 11 is delayed in the time-delay element 16b. With the time-delay element 16a switched off, the initial pulse is led without a delay to the sound transducer 5a that is situated ahead when seen in the direction of sound intromission. As is seen from the timing diagram in FIG. 6, this produces a time delay with a value T for the sound transducer 5b that is situated behind in the direction of sound intromission. Given the correct choice of the time difference or delay T, a synchronous sound wave front 21, that is symbolized in the middle portion of FIG. 8, is formed from sound waves 17 and 18 of the sound transducers 5a and 5b. The same phase angle of the two sound waves 17, 18 that are synchronized to form a sound wave front 21 may be seen in the timing diagram of FIG. 7. Due to the time delay, the sound amplitudes add together to form a larger total amplitude, with the result that the testing sensitivity turns out to be substantially higher than in the case of a single sound transducer in an angle-beam probe of the same overall height. If the time-delay elements 16a and 16b are omitted, the time delay of the initial pulse which is shown in FIG. 6 can also be achieved by transmitting the initial pulses from the distributor 10 with a time delay. If a pulse were to be applied simultaneously to the sound transducers 5a and 5b, the sound waves 17 and 18 would run separately in time into the test specimen 8, as is indicated symbolically in the outer portions of FIG. 8, and therefore the pulses would behave like pulses emanating from two individual sound transducers. The success aimed for is achieved only by delaying the sound pulses, in accordance with the invention.

The sound waves returning, for example, from a reflector (a material defect) reach the receiver 5c earlier than the receiver 5d. It is possible to add the signals in the combining unit 14 by appropriately controlling the delay in the time delay elements 16c and 16d.

I claim:

1. A method for operating an ultrasonic angle-beam probe, which comprises:

providing one wedge surface on each of at least two approach wedges;

aligning the at least two approach wedges in front and rear positions as seen in a sound intromission direction into a test specimen;

placing at least one sound transducer on each respective wedge surface defining at least one front and at least one rear sound transducer;

connecting at least one of a pulse generator and a sound evaluator to each sound transducer;

connecting a device to at least one sound transducer for influencing an echo time of sound outside the test specimen; and irradiating sound by firstly transmitting an initial pulse from the rear sound transducer, transmitting an initial pulse from the front sound transducer after a prescribable time interval, and delaying a received pulse running from the test specimen to the sound evaluator as a function of an angle of the sound intromission.

2. A method for operating an ultrasonic angle-beam probe, which comprises:

providing one wedge surface on each of at least two approach wedges;

aligning the at least two approach wedges in front and rear positions as seen in a sound intromission direction into a test specimen;

placing at least one sound transducer on each respective wedge surface defining at least one front and at least one rear sound transducer;

connecting at least one of a pulse generator and a sound evaluator to each sound transducer;

connecting a device to at least one sound transducer for influencing an echo time of sound outside the test specimen; and irradiating the sound by simultaneously transmitting initial pulses of the individual sound transducers, delaying echo times with respect to one another by a prescribable extent, and delaying a received pulse coming from the test specimen to the sound evaluator as a function of an angle of the sound intromission.

* * * * *